(12) United States Patent
Yokoyama et al.

(10) Patent No.: US 10,669,525 B2
(45) Date of Patent: Jun. 2, 2020

(54) METHOD FOR PRODUCING THREE-DIMENSIONAL CELL AGGREGATES

(71) Applicants: PUBLIC UNIVERSITY CORPORATION YOKOHAMA CITY UNIVERSITY, Yokohama-shi, Kanagawa (JP); OSAKA UNIVERSITY, Suita-shi, Osaka (JP); NATIONAL UNIVERSITY CORPORATION NAGOYA UNIVERSITY, Nagoya-shi, Aichi (JP)

(72) Inventors: Utako Yokoyama, Yokohama (JP); Yoshihiro Ishikawa, Yokohama (JP); Makoto Kaneko, Suita (JP); Shinya Sakuma, Nagoya (JP); Fumihito Arai, Nagoya (JP)

(73) Assignees: PUBLIC UNIVERSITY CORPORATION YOKOHAMA CITY UNIVERSITY, Yokohama-Shi (JP); OSAKA UNIVERSITY, Suita-Shi (JP); NATIONAL UNIVERSITY CORPORATION NAGOYA UNIVERSITY, Nagoya-Shi (JP)

(*) Notice: Subject to any disclaimer, the term of this patent is extended or adjusted under 35 U.S.C. 154(b) by 0 days.

(21) Appl. No.: 15/515,013

(22) PCT Filed: Sep. 29, 2015

(86) PCT No.: PCT/JP2015/077447
§ 371 (c)(1),
(2) Date: Mar. 28, 2017

(87) PCT Pub. No.: WO2016/052472
PCT Pub. Date: Apr. 7, 2016

(65) Prior Publication Data
US 2017/0218329 A1    Aug. 3, 2017

(30) Foreign Application Priority Data

Sep. 29, 2014 (JP) ................................ 2014-198224
Feb. 23, 2015 (JP) ................................ 2015-033064

(51) Int. Cl.
*C12M 1/24* (2006.01)
*C12M 1/00* (2006.01)
(Continued)

(52) U.S. Cl.
CPC ........... *C12N 5/0062* (2013.01); *C12M 23/06* (2013.01); *C12M 23/08* (2013.01); *C12M 23/10* (2013.01);
(Continued)

(58) Field of Classification Search
None
See application file for complete search history.

(56) References Cited

U.S. PATENT DOCUMENTS 6,528,052 B1 * 3/2003 Smith ................. A61F 2/30756
424/93.7
2003/0036196 A1   2/2003 Okano et al.
(Continued)

FOREIGN PATENT DOCUMENTS

EP       1266960 A1    12/2002
JP    63-226204 A     9/1988
(Continued)

OTHER PUBLICATIONS

International Search Report (PCT/ISA/210) issued in PCT/JP2015/077447, dated Dec. 28, 2015.
(Continued)

*Primary Examiner* — Allison M Fox
(74) *Attorney, Agent, or Firm* — Birch, Stewart, Kolasch & Birch, LLP (57) ABSTRACT

Means which enables preparation of a thick cell aggregate by a simple process without an operation of detaching and stacking of cells is disclosed. The method for preparing a three-dimensional cell aggregate by the present invention comprises: a cell encasing step of placing a cell suspension
(Continued)

in a cell container; and a pressure application step of applying pressure to cells in the container. The cell encasing step and the pressure application step may be carried out a plurality of times. By the present invention, a thick, robust cell aggregate can be obtained by a simple operation of applying pressure to a cell suspension or a medium containing cells. Since the method does not require an operation of stacking a plurality of cell sheets, the cells are hardly damaged, and the conditions of the cells can be favorably maintained, so that the cells can be advantageously used as a tissue piece for transplantation.

11 Claims, 10 Drawing Sheets (51) Int. Cl.
| | |
|---|---|
| C12M 3/00 | (2006.01) |
| C12N 5/00 | (2006.01) |
| C12N 5/077 | (2010.01) |
| C12M 1/12 | (2006.01) |
| C12M 1/22 | (2006.01) |
| C12M 1/34 | (2006.01) |

(52) U.S. Cl.
CPC ............ *C12M 23/38* (2013.01); *C12M 41/40* (2013.01); *C12N 5/0661* (2013.01); *C12M 3/00* (2013.01)

(56) References Cited

U.S. PATENT DOCUMENTS

| | | |
|---|---|---|
| 2003/0224510 A1 | 12/2003 | Yamaguchi et al. |
| 2009/0111180 A1 | 4/2009 | Vilendrer et al. |
| 2009/0148876 A1 | 6/2009 | Dodge |
| 2010/0041134 A1 | 2/2010 | Forgacs et al. |

FOREIGN PATENT DOCUMENTS

| | | |
|---|---|---|
| JP | 2001-238663 A | 9/2001 |
| JP | 2003-289851 A | 10/2003 |
| JP | 2003-339369 A | 12/2003 |
| JP | 2004-283010 A | 10/2004 |
| JP | 2010-22269 A | 2/2010 |
| JP | 2010-148401 A | 7/2010 |
| JP | 2011-525376 A | 9/2011 |
| WO | WO 01/68799 A1 | 9/2001 |

OTHER PUBLICATIONS

Written Opinion (PCT/ISA/237) issued in PCT/JP2015/077447, dated Dec. 28, 2015.
Abe, F., "Study on Dynamics of Biomembranes and Membrane Proteins as Investigated in Relation to Pressure," Readout (Dec. 2009), No. 35, pp. 16-20, With English translation.
Angele et al., "Cyclic hydrostatic pressure enhances the chondrogenic phenotype of human mesenchymal progenitor cells differentiated in vitro," Journal of Orthopaedic Research (2003), vol. 21, pp. 451-457.
Hall et al., "The Effects of Hydrostatic Pressure on Matrix Synthesis in Articular Cartilage," Journal of Orthopaedic Research (1991), vol. 9, No. 1, pp. 1-10.
Matsumoto et al., "Effect of Compressive Stress on the Extracellular Matrix in Human Fibroblasts and Endothelial Cells," J. Jpn. Acad. Nurs. Sci. (2009), vol. 29, No. 3, pp. 3-12, with English abstract.
Parkkinen et al., Effects of Cyclic Hydrostatic Pressure on Proteoglycan Synthesis in Cultured Chondrocytes and Articular Cartilage Explants, Archives of Biochemistry and Biophysics (Jan. 1993), vol. 300, No. 1, pp. 458-465.
Suh et al., "Intermittent sub-ambient interstitial hydrostatic pressure as a potential mechanical stimulator for chondrocyte metabolism," Osteoarthritis and Cartilage (1999), vol. 7, pp. 71-80.
Extended European Search Report dated Apr. 24, 2018, for European Application No. 15846123.6.

* cited by examiner

H9C2 cells (Rat heart-derived myoblasts)

without pressurization 17 h       110-180 kPa   17 h

Fig.3

NIH3T3 cells (Mouse embryo-derived fibroblasts)

without pressurization 17 h       110-180 kPa   17 h

METHOD FOR PRODUCING THREE-DIMENSIONAL CELL AGGREGATES

TECHNICAL FIELD

The present invention relates to a method for preparing a three-dimensional cell aggregate.

BACKGROUND ART

In the field of regenerative medicine, research and development of three-dimensional tissues using biodegradable polymer scaffolds and cell sheets using no scaffolds are in progress. In recent years, cell sheet technologies are attracting special attention. In preparation of a cell sheet, it is necessary to put a cell suspension into cell culture vessels, grow the cells in an incubator, collect the grown monolayer cell sheets from the surfaces of the culture vessels, and stack the cell sheets. Since most cells have a nature of stopping their growth upon contacting, it is necessary to detach cell sheets from vessels and stack them in order to prepare a cell sheet having more than a certain thickness. However, protease is required to collect cells having adhesive capacity from the vessels, which leads to decomposition of the cell tissue into separate cells, and thus it has been difficult to collect cells as a normal cell tissue.

The technique by Patent Document 1 solved the above-described problem. Patent Document 1 discloses a technique in which cultured cells are collected as a cell sheet simply by using a "temperature-responsive cell culture apparatus" and changing the culture temperature. Since the cultured cells obtained have not undergone enzyme treatment, they have the advantage that they can be collected as a single sheet without destroying proteins present between cells.

However, for preparation of a cell sheet having more than a certain thickness, even the technique according to Patent Document 1 requires a laborious operation of stacking a plurality of monolayer cell sheets. There have been only a very limited number of reports in which cells were successfully formed into a three-dimensional multilayered sheet by a simple process. There has been no technique that can be used at a practical level.

PRIOR ART DOCUMENT(S)

Patent Document(s)

Patent Document 1: WO 01/068799

SUMMARY OF THE INVENTION

Problems to be Solved by the Invention

An object of the present invention is to provide means for enabling preparation of a thick cell aggregate by a simple process without an operation of detaching and stacking of cells.

Means for Solving the Problems

The present inventors have intensively studied to discover that a thick sheet-shaped cell aggregate can be obtained simply by applying pressure to a cell suspension or a medium containing cells, and that, by carrying out addition of cells and application of pressure a plurality of times, a cell aggregate in which cells adhere to and aggregate with each other to form a sheet shape with a sufficient strength can be obtained, thereby completing the present invention.

That is, the present invention provides a method for preparing a three-dimensional cell aggregate, said method comprising: a cell encasing step of placing a cell suspension in a cell container; and a pressure application step of applying pressure to cells in said container. The present invention also provides a cell sheet comprising a three-dimensional cell aggregate prepared by the above-described method of the present invention. The present invention further provides a device for preparing a three-dimensional cell aggregate, said device comprising: a cell container for receiving a cell suspension therein; and pressure application means for applying pressure to cells in said cell container continuously, periodically, or intermittently, or in a manner in which a plurality of these modes are combined.

Effect of the Invention

By the present invention, a thick, robust cell aggregate can be obtained by a simple operation of applying pressure to a cell suspension or a medium comprising cells. Without using a special culture apparatus such as the one used in the technique described in Patent Document 1, a sheet-shaped cell aggregate can be prepared using a system having a simple constitution. Since the operation of stacking a plurality of cell sheets is not necessary, cells are hardly damaged, and the cells can be kept in a favorable state, so that the cells can be advantageously used as a tissue piece for transplantation. The cell aggregate obtained by the method of the present invention is expected to be practically used not only as a tissue piece for transplantation, but also in a variety of fields such as the field of drug discovery including evaluation of drug efficacy and drug screening, and the field of foods including artificial meat (cultured meat).

BRIEF DESCRIPTION OF THE DRAWINGS

FIG. 11-1 shows the results of investigating the influence of the period of the pressurization cycle on cell aggregates. Human umbilical arterial smooth muscle cells were subjected to pressurization treatment for 20 hours by pressurization cycles of 110 kPa-180 kPa with different periods. Thereafter, the expression levels of extracellular matrix genes (fibrillin 1, fibrillin 2, fibulin 4, fibulin 5, LOX, LOX-like protein 1) were investigated. $*p<0.05$, $***p<0.001$ vs 101 kPa.

FIG. 11-2 shows the results of investigating the influence of the period of the pressurization cycle on the cell aggregate. Human umbilical arterial smooth muscle cells were subjected to pressurization treatment for 20 hours by pressurization cycles of 110 kPa-180 kPa with different periods. Thereafter, the expression levels of extracellular matrix genes (collagen I, collagen III, fibronectin) were investigated. $**p<0.01$ vs 101 kPa.

MODE FOR CARRYING OUT THE INVENTION

The method for preparing a three-dimensional cell aggregate by the present invention comprises: a cell encasing step of placing a cell suspension in a cell container; and a pressure application step of applying pressure to cells in the container.

The pressure application step may be carried out immediately after placing a cell suspension in the container, or may be delayed by a certain amount of time until cells in the suspension precipitate to the bottom of the container. That is, the present invention may comprise, between the cell encasing step and the pressure application step, a non-pressurization step of maintaining the cell suspension without pressurization. In cases where the non-pressurization step is carried out, the length of the non-pressurization period is not limited, and may be appropriately set depending on the amount, the type, and the like of the cells used. Normally, most of the cells in the cell suspension precipitate when the cell suspension is left to stand for about 30 minutes to several hours. However, the cell suspension may be left to stand for not less than 12 hours, for example, not less than about 20 hours. The upper limit of the length of the non-pressurization period is also not limited. It is normally not more than about several days, for example, not more than about 72 hours.

In the present invention, the cell encasing step and the pressure application step may be carried out two or more times repeatedly. That is, when the "cell encasing step→pressure application step" process is regarded as one routine, not less than two routines may be carried out. In cases where the cell encasing step and the pressure application step are carried out two or more times, the conditions of the pressurization treatment (pressurization pattern) may be the same or different among the pressure application steps. By repeating the addition of cells and the application of pressure, a thicker and more robust cell aggregate can be prepared. In cases where two or more routines are carried out, the number of times of the routines is not limited. The cell encasing step and the pressure application step may be carried out a large number of times for several weeks or for a longer period. As described above, the non-pressurization step may be included between the cell encasing step and the pressure application step. The length of time of the non-pressurization step may also be the same or different among the routines.

The cells used in the present invention are animal cells, preferably mammalian cells such as human cells. The type of the cells is not limited, and smooth muscle cells, cardiac muscle cells, fibroblasts, myoblasts, cartilage cells, osteoblasts, and the like may be used. The cells may be those prepared by differentiation of pluripotent cells excluding human embryonic stem cells, such as induced pluripotent stem cells, or stem cells or precursor cells of various tissues.

In cases where a cell aggregate for use as a tissue to be transplanted to a human patient is prepared, cells collected from the patient or another individual may be cultured, grown, and allowed to differentiate if necessary, to prepare a cell suspension. The cell suspension to be used may be prepared by culturing the cells by monolayer culture according to a conventional method in a culture vessel such as a petri dish, detaching the resulting monolayer cells and dispersing the monolayer into cells by treatment with an enzyme such as trypsin, performing centrifugation, removing the supernatant, and then adjusting the cell density appropriately. The medium in which cells are dispersed may be a culture medium commonly used for cell culture, or a buffer such as HEPES buffer (4-(2-HydroxyEthyl)-1-PiperazineEthaneSulfonic acid) or phosphate buffered saline.

The cell density in the cell suspension is adjusted to a sufficiently high cell density. The appropriate cell density may vary depending on the shape and the size of the cell container, and the size of the cell itself. In general, the sufficient amount of the cells contained in the cell suspension may be larger than the amount with which a monolayer can be formed on the area of the bottom of the cell container in the direction of gravity during the pressure application. In cases where the cell container has a cylindrical shape such as a syringe shape, and where the container is in a state where it is placed horizontally during the pressure application, the area of the bottom in the direction of gravity corresponds to the inner area of the lower half of the syringe that is placed horizontally. In cases where a cell aggregate is prepared from cultured smooth muscle cells in a 1-mL syringe, a cell density of not less than 300,000 cells/mL is sufficient for the preparation of a three-dimensional cell aggregate. Also in cases where the cell container and the cells used are different from these, a cell suspension with a cell density corresponding to not less than 1000 cells per 1 $cm^2$, for example, not less than about 100,000 cells per 1 cm², or not less than about 250,000 cells per 1 cm², may be sufficiently used. Although the upper limit of the cell density is not limited, the cell density is usually not more than 10,000,000 cells per 1 cm².

The cell suspension may be prepared with only one kind of cells, or with a mixture of two or more kinds of cells. For example, in cases where a cardiac muscle tissue is to be produced, the cell suspension may be prepared with a mixture of cardiac muscle cells and vascular endothelial cells. In cases where the cell encasing step and the pressure application step are carried out a plurality of times, the type of the cells to be added into the cell container may be changed. An artificial tissue may be constructed by stacking different cells using, for example, fibroblasts for the first two layers, smooth muscle cells for the next four layers, and endothelial cells for the uppermost layer.

The cell container is not limited as long as its material does not adversely affect living cells, and as long as the container has a strength which provides resistance to the pressurization treatment. The shape of the cell container is also not limited, and the container may be a container having a cylindrical shape such as a syringe or a tube; a container having a flask-like shape; or a container having a flat shape such as a culture dish. The cell container may be, for example, a non-sealed container having an opening communicating with the gas phase outside the container. In cases where a non-sealed, lidded container is used, the gap between the lid and the main body of the container acts as the opening, and allows the communication with the gas phase outside the container. However, since, in the present invention, the pressure application is usually carried out in a state where the cell container is left to stand, a lid is not always necessary for the cell container. The pressure application is usually carried out in a state where the cell container is placed in a pressure vessel that is resistant to high pressure. By sending compressed air into the pressure vessel, pressure can be applied to the cells (medium containing the cells) in the cell container. As mentioned below, although it is also possible to send a high-pressure medium into the cell container so as to apply pressure to the cells, the pressurization method using compressed air is more preferred since such a method can be carried out with a simple system configuration and makes it possible to more freely select the shape of the cell container.

The inner wall of the cell container does not necessarily have to be subjected to surface treatment for cell adhesion (collagen coating, polylysine coating, or the like). In cases where a thin sheet-shaped cell aggregate or a non-sheet-shaped cell aggregate is to be produced, the inner wall without such surface treatment for cell adhesion makes it easier to harvest the cell aggregate after the pressurization treatment. As mentioned below, by carrying out the cell encasing step and the pressure application step two or more times repeatedly, a thicker and more robust cell aggregate can be produced. In cases where a sheet-shaped cell aggregate is produced in such a method, the inner wall of the cell container may be subjected to surface treatment for cell adhesion. By allowing the first cell layer to adhere to the inner wall of the container, and then sequentially laying cell layers thereon, a thicker and still more robust cell aggregate can be prepared. The cell aggregate prepared can be easily recovered from the container by manually peeling it off.

In the absence of artificially-applied pressure, the cell suspension or the medium containing the cells is under atmospheric pressure. In the present invention, "application of pressure to cells in a container" means that the medium containing the cells is placed under a pressure higher than atmospheric pressure. In the present description, "atmospheric pressure" means a pressure of about 100 kPa to about 101 kPa. The state where the cell suspension or the medium containing the cells is under only atmospheric pressure may be expressed as "non-pressurized" state.

In the method of the present invention, the pressure applied to the cell suspension or the medium containing the cells may be not less than about 102 kPa, preferably not less than about 110 kPa, for example, not less than 150 kPa, or about 180 kPa. The upper limit of the pressure is not limited, and may be appropriately selected depending on the type of the cells. The pressure is usually not more than 100 MPa, or may be, for example, not more than about 1000 kPa, not more than about 500 kPa, not more than about 400 kPa, or not more than about 300 kPa.

The length of the pressurization treatment is not limited, and may be appropriately set depending on the type of the cells used, the cell number, and/or the like. Usually, a pressurization treatment for about several ten minutes is sufficient for allowing aggregation and adhesion of the cells, and thus a three-dimensional cell aggregate can be obtained. The length of the pressurization treatment in each pressure application step may be, for example, not less than about 30 minutes, not less than about 90 minutes, not less than about 3 hours, or not less than about 5 hours. The upper limit of the length of the pressurization treatment in each pressure application step is also not limited. The length of the pressurization treatment in each pressure application step is usually not more than about several days, and may be, for example, not more than about 72 hours, or not more than about 48 hours. However, since a desired cell aggregate can be obtained even in cases where the pressure application step is carried out for a longer period, the upper limit of the length of each pressurization treatment is not limited to those described above, and the pressurization treatment may be carried out for a period of more than several days, for example, for a period of about one or two months. Although replacement of the medium (culture medium or buffer) of the cell suspension is not necessarily required in the present invention, replacement of the medium may be carried out, if necessary, during the pressurization treatment or at another appropriate time for maintaining an environment preferred for the cells.

The pressurization pattern is not limited, and the pressurization may be carried out continuously or periodically. Pressure may be continuously applied at a constant intensity through the pressurization treatment period, or the pressure applied may be changed at intervals of several seconds to several minutes or several hundred seconds to perform periodic pressurization treatment. A pressurization pattern based on combination of three or more kinds of pressure (for example, 300 kPa→atmospheric pressure→150 kPa→atmospheric pressure) may be employed. In each pressure application step, periodic pressurization with the same cycle may be continued, or the pressurization pattern may be changed during the step. A preferred pressurization pattern can be appropriately selected depending on the type of the cells used, the cell number, and/or the like. In the present invention, for example, "application of a pressure of 180 kPa for 90 minutes" means not only continuous application of a pressure of 180 kPa to the cells in the medium for 90 minutes, but also repeating of pressurization at 180 kPa for several seconds to several hundred seconds and pressurization at a lower pressure or non-pressurization (atmospheric pressure) for several seconds to several hundred seconds, and includes e.g. carrying out a cycle of "application of a pressure at 180 kPa for 10 seconds→atmospheric pressure for 10 seconds" for 90 minutes.

The temperature during the pressurization treatment may be appropriately set depending on the type of the cells used. Usually, temperature conditions employed for culturing the cells used are employed. In cases of animal cells, the temperature normally used is about 30° C. to 40° C., and, in cases of human somatic cells, the temperature may be about 35° C. to 38° C. However, the temperature is not limited, and may be lowered to about room temperature or a low temperature which does not cause freezing (about 15° C.). In cases where the non-pressurization step is included, the temperature during the non-pressurization step may be the same as the temperature during the pressure application step, or may be different from the temperature during the pressure application step.

Figure 1:
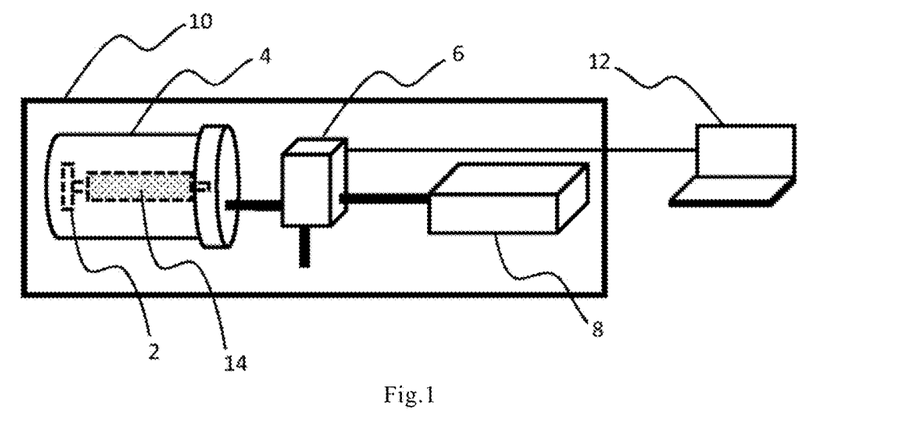
FIG. 1 shows a schematic diagram showing an example of a system for carrying out the method of the present invention.

An example of the system or device for carrying out the method of the present invention is shown in FIG. 1. In the following description, the term "cell suspension" includes not only liquids in a state where cells are dispersed in the entire medium, but also liquids in a state where cells in the medium have precipitated downward to make the cell density uneven.

In the mode shown in FIG. 1, the pressure application means for applying pressure to cells in the cell container includes a compressor 8 and a regulator 6. A pressure vessel 4 for holding a cell container 2 therein is connected to the compressor 8 through the regulator 6, and these are placed in an incubator 10 as a closed space. The regulator 6 is connected to a computer 12 placed outside the incubator 10, and the intensity and the pattern of the pressure applied to a cell suspension 14 in the cell container 2 are controlled by instructions from the computer 12. In an example shown in FIG. 1, the pressure application means and the pressure vessel holding the cell container therein are held in the closed space, but in the present invention, their arrangement is not limited as long as at least the cell container is held in the closed space. The closed space herein means a space where the composition of the gas and the temperature in the space can be controlled independently of those in the outside thereof.

The pressure vessel 4 has an appropriate internal shape that is suitable for the cell container 2 used. The cell container 2 held in the pressure vessel 4 is a non-sealed container (in an example shown in FIG. 1, the cell container 2 is a non-sealed syringe whose tip is open), and the cell suspension 14 communicates with the outside (the gas phase in the incubator 10) through the regulator 6. By sending air in the incubator 10 compressed by the compressor 8 into the pressure vessel 4, pressurization treatment is carried out. In cases of non-pressurization (atmospheric pressure), the pressure may be set to about 100 kPa to 101 kPa.

As mentioned above, in cases where the cell encasing step and the pressure application step are carried out a plurality of times to prepare a cell aggregate, the non-pressurization step may be carried out between the cell encasing step and the pressure application step. This system therefore allows continuous pressurization, periodic pressurization, or pressurization in a manner in which their combination is intermittently carried out. That is, in this system, the computer 12 can give instructions such that pressure is applied continuously, periodically, or intermittently, or in a manner in which a plurality of these modes are combined.

The $CO_2$ concentration in the closed space (in the incubator) may be a concentration that is used for culturing the cells in a normal manner. In cases of human somatic cells, the $CO_2$ concentration is generally set to 5.0%. During the pressure application step, the $CO_2$ concentration in the incubator 10 may be adjusted such that the pH of the cell suspension is appropriately maintained. That is, the system shown in FIG. 1 may have means for adjusting the $CO_2$ concentration in the closed space (in the incubator), i.e. the $CO_2$ concentration in the air to be sent into the pressure vessel. However, it has been confirmed that, even in cases where the pressure application is carried out by repeating a cycle of pressurization for several minutes→non-pressurization for several minutes, the pH of the cell suspension can be appropriately maintained by keeping the $CO_2$ concentration in the incubator 10 constant without fluctuating it. Thus, the control of the $CO_2$ concentration is not necessarily required. For example, while the pressure application step is carried out on human somatic cells, the $CO_2$ concentration in the incubator 10 may be kept at 5.0%. In cases where the $CO_2$ concentration is controlled, the range within which the $CO_2$ concentration is controlled during the pressurization treatment is not limited, and may be appropriately selected depending on the type of the cells, intensity of the pressure, and/or the like. In cases where human somatic cells are used and a pressure of about 180 kPa is applied, the $CO_2$ concentration during the pressure application step may be controlled within the range of about 3.0% to 5.0%, for example, about 3.5% to 5.0%. For example, in cases where periodic pressurization by "pressurization→non-pressurization" is carried out, the $CO_2$ concentration may be controlled such that the $CO_2$ concentration during the non-pressurization is about 5.0%, and the $CO_2$ concentration during the pressurization is about 3.5%. Or, the $CO_2$ concentration during the pressure application step may be kept constant at a concentration slightly lower than that during ordinary cell culture. For example, in cases where human somatic cells are used and the non-pressurization step is employed between the cell encasing step and the pressure application step, the $CO_2$ concentration during the non-pressurization step may be kept at 5.0%, and the $CO_2$ concentration during the pressure application step may be kept constant at not less than 3.0% and less than 5.0% (e.g., at about 3.5%).

Or, the system may have a constitution as follows. That is, as pressure application means, a container for holding a medium, and a pump, are arranged instead of the compressor 8, and a liquid transfer line which connects them to the inside of the cell container 2 held in the pressure vessel 4 is provided. In this constitution, pressure is applied to the medium to send the medium into the cell container 2, thereby carrying out the pressurization treatment. A porous membrane having pores with a size that does not allow the cells held in the container to pass therethrough may be arranged at the connecting portion between the liquid transfer line and the cell container, so that the cells can be prevented from escaping to the outside of the cell container due to backflow or the like. In addition, in this constitution, the pressure vessel may be integrated with the cell container to be used as a cell container with resistance to high pressure.

In cases where the pressurization treatment is carried out in a short time, replacement of the medium of the cell suspension during the pressurization treatment is not necessary, and the system can have a simple constitution.

In cases where the pressurization treatment is carried out for a long time, a system constitution in which automatic or manual replacement of the medium can be carried out as needed may be employed. For example, in cases where a cell aggregate is prepared by carrying out the cell encasing step and the pressure application step a plurality of times, replacement of the medium can be carried out at the same time by removing part of the medium after pressurization treatment and newly adding the cell suspension. In cases of a constitution in which the pressurization treatment is carried out by sending the medium, instead of air, into the cell container 2, a waste line that allows discarding of the medium in the cell container 2 to the outside of the container, and pressure control means on the waste line such as a regulator for controlling the hydrostatic pressure of the medium, may be arranged, to provide a constitution in which the medium can be replaced not only at the time of addition of the cell suspension, but also at any other time. At the connecting portion between the waste line and the cell container 2, a porous membrane may be arranged similarly to the connecting portion between the liquid transfer line and the cell container 2. However, even in cases where the treatment is carried out for a period of as long as about 1 month, replacement of the medium does not have to be carried out frequently, and partial replacement of the medium at the time of addition of the cell suspension may be sufficient.

By the method of the present invention, a cell tissue body (cell aggregate or cell agglomerate) consisting essentially of cells (cells and substances produced from the cells) can be produced without using a three-dimensional scaffolding such as a porous scaffolding composed of a polymer, biomolecule or the like that has been conventionally and indispensably used for production of a three-dimensional cell aggregate. In the field of tissue engineering for regenerative medicine, research and development of three-dimensional tissues using a three-dimensional scaffolding of a biodegradable polymer, and cell sheets produced without using a three-dimensional scaffolding, are in progress. By the present invention, aggregation and adhesion of cells to each other can be promoted by only performing pressurization treatment without coexistence of a porous three-dimensional scaffolding in the cell suspension, to obtain a thick cell cluster. However, depending on the purpose of use of the cell aggregate, a certain scaffolding may be used.

The three-dimensional cell aggregate obtained by the method of the present invention can be utilized as it is as a cell sheet. In the conventional methods for producing a cell sheet, the operation of stacking of a plurality of monolayer cultured cells is necessary for production of a thick multilayer cell sheet. In contrast, in the method of the present invention, operation of sequentially stacking prepared monolayer cells is not carried out, so that the production process is simple, and the damage on the cells can be largely reduced. Since the size and the shape of the cell aggregate may be influenced also by the shape of the cell container used, it is also possible to control the size and the shape of the cell aggregate by selection of the cell container.

EXAMPLES

The present invention is described below more concretely by way of Examples. However, the present invention is not limited to these Examples.

1. Preparation of Cell Aggregate by Pressure Application 1

Cells such as human umbilical arterial smooth muscle cells were subjected to monolayer culture in a petri dish, and the resulting monolayer cells were detached by treatment with trypsin, followed by dispersing the cells in DMEM medium supplemented with 10% bovine serum. After centrifugation, the supernatant was removed, and the cell density was appropriately adjusted to one million cells/mL to several million cells/mL.

Figure 2:
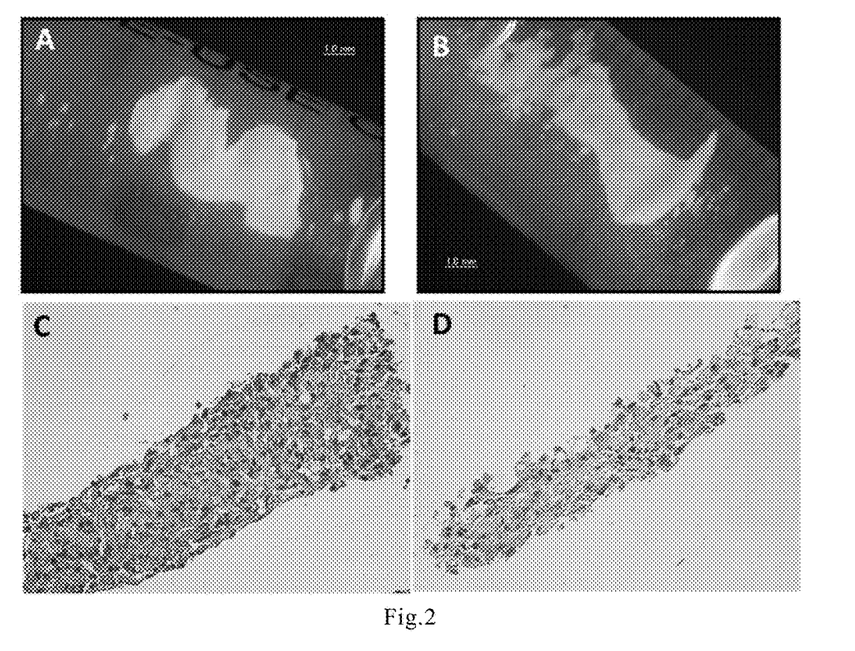
FIG. 2 shows the results of incubating a human smooth muscle cell suspension for 15 hours with pressurization treatment or without pressurization treatment. (A) Cells obtained with pressurization treatment; (B) cells obtained without pressurization treatment; (C) an image of a stained section of cells obtained with pressurization treatment; (D) an image of a stained section of cells obtained without pressurization treatment.

Using the system shown in FIG. 1, pressurization treatment of the cells was carried out. In a 1-mL syringe, 300 µL of human smooth muscle cell suspension with a cell density of 1,000,000 cells/mL prepared as described above was placed, and the syringe was then held in a pressure vessel in an incubator. The conditions in the incubator were set at 5% $CO_2$, 37° C., and the $CO_2$ concentration was controlled at 3.6% to 5.0% during the pressurization treatment. The pressurization treatment was carried out by repeating "180 kPa for 10 seconds→110 kPa for 10 seconds". At Minute 90 and Hour 15 during the course of the pressurization treatment, the conditions of the cells in the syringe were observed. As a result, at Minute 90 during the pressurization treatment, the cells were found to be aggregating and adhering to each other to form a sheet-like shape. FIG. 2A shows a cell cluster observed at Hour 15 during the pressurization treatment.

Similarly, 300 µL of the smooth muscle cell suspension with a cell density of 1,000,000 cells/mL was placed in a 1-mL syringe, and the syringe was then incubated for 15 hours without pressurization treatment. The resulting cells were compared with the cells obtained after the 15-hour pressurization treatment described above.

FIG. 2B shows cells obtained without the pressurization treatment. FIG. 2C and FIG. 2D show images of HE-stained sections of the obtained cell clusters. Since a high-density cell suspension was used, cells aggregated with each other to some extent even without the pressurization treatment. However, as shown by the HE-stained image, the cell cluster had only low robustness, and its thickness was small, so that the cell cluster was unusable as a cell sheet (FIG. 2B and FIG. 2D). In contrast, in the case where the pressurization treatment was carried out, most of the cells in the suspension aggregated with each other to produce a cell cluster having a thickness of not less than 100 µm (FIG. 2A, FIG. 2C). Nuclei were also found inside the cell cluster. The cell cluster was highly robust, in which the cells were tightly aggregating. This cell cluster was further cultured at 37° C. for up to 24 hours, and then observed. As a result, the cells were found to be retaining the shape as a sheet-shaped cell aggregate without causing disaggregation of the cells and breakage of the cell cluster.

Figure 3:
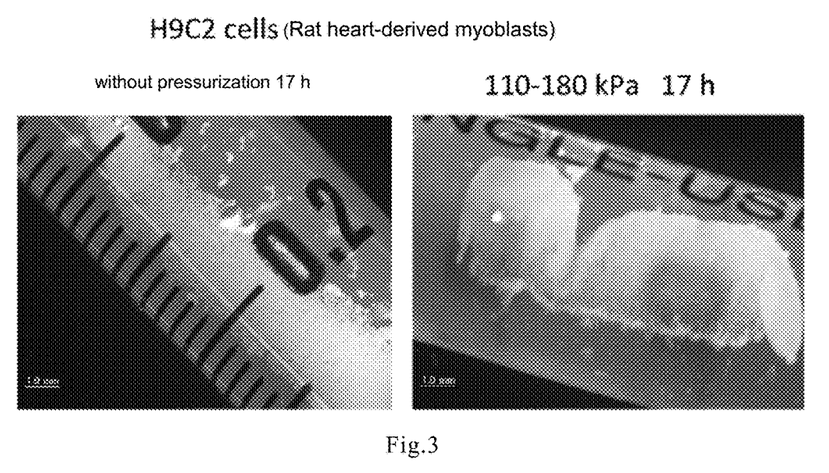
FIG. 3 shows the results of incubating rat heart-derived myoblasts H9C2 for 17 hours with pressurization treatment or without pressurization treatment.
Figure 4:
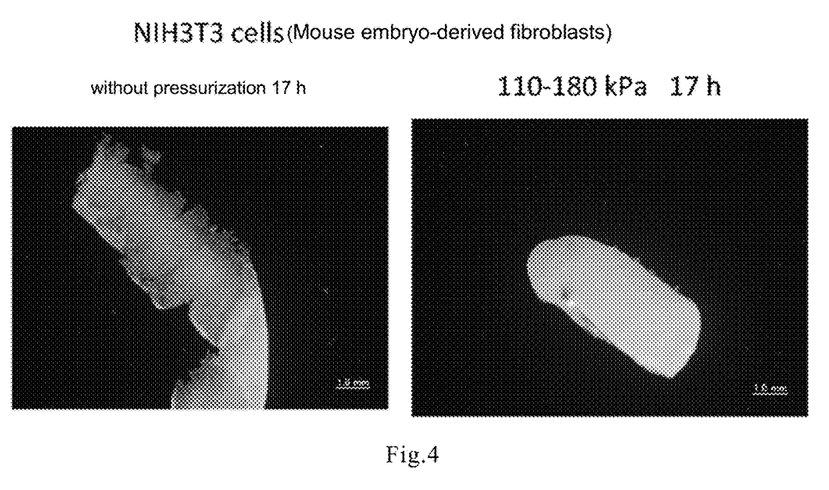
FIG. 4 shows the results of incubating mouse embryo-derived fibroblasts NIH3T3 for 17 hours with pressurization treatment or without pressurization treatment.

FIG. 3 shows photographs of cells obtained by subjecting a suspension of rat heart-derived myoblasts H9C2 to pressurization treatment (right) or to incubation without pressurization treatment (left). FIG. 4 shows photographs of cells obtained by subjecting a suspension of mouse embryo-derived fibroblasts NIH3T3 to pressurization treatment (right) or to incubation without pressurization treatment (left). It could be confirmed that a highly robust sheet-shaped cell cluster can be obtained with these cells similarly to the smooth muscle cells. The density of the cell suspension was 1,950,000 cells/mL in the case of the rat heart-derived myoblasts H9C2, and 3,150,000 cells/mL in the case of the mouse embryo-derived fibroblasts NIH3T3. The volume of the suspension placed in the syringe was 300 µL in both cases. The pressurization treatment was carried out by repeating "180 kPa for 10 seconds→110 kPa for 10 seconds". The treatment time was 17 hours.

2. Preparation of Cell Aggregate by Pressure Application 2

Figure 5:
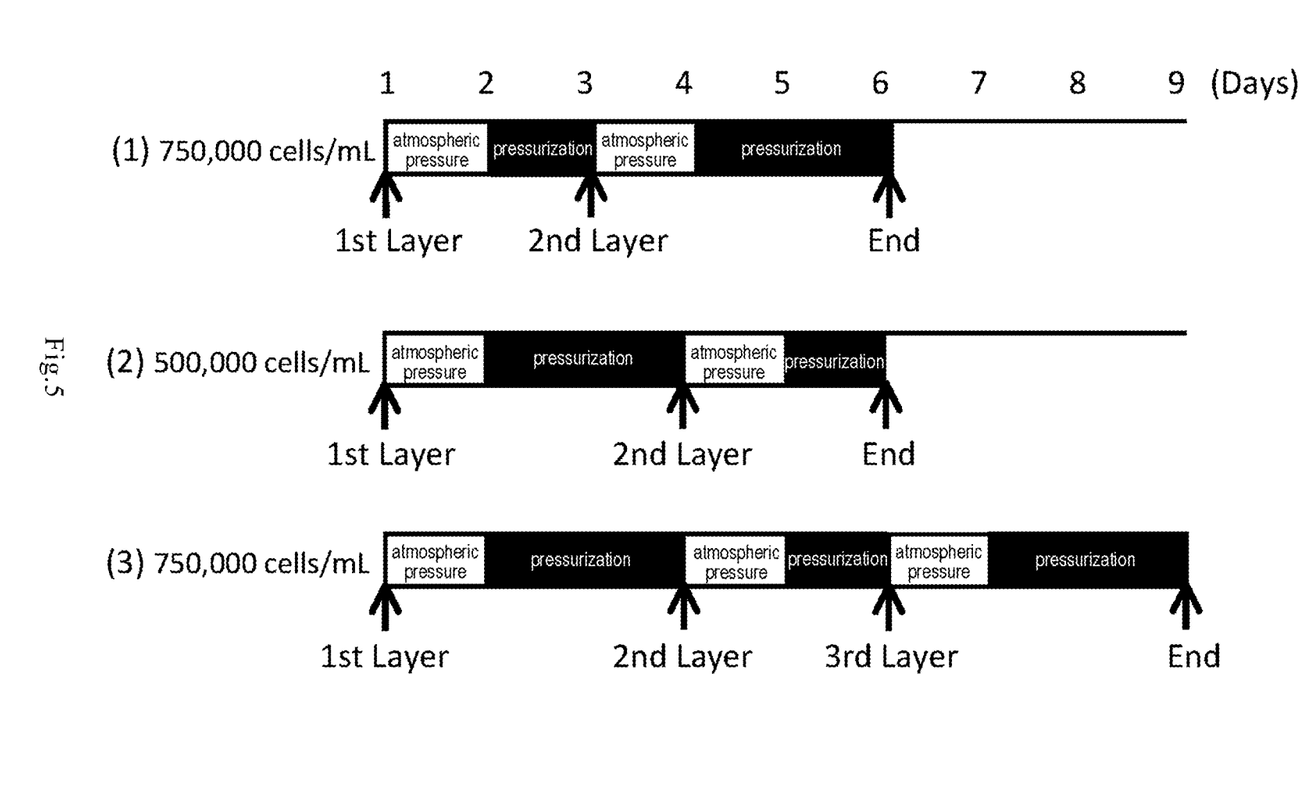
FIG. 5 shows a diagram illustrating the time course of a preparation method carried out in Examples, wherein addition of cells and application of pressure were repeated.

Using human smooth muscle cells, a method in which addition of cells to the cell container and application of pressure were repeated (FIG. 5, the following (1) to (3)) was carried out to prepare cell aggregates. As the cell container, a square or circular glass culture dish was used. The culture dish was coated with fibronectin. The pressurization pattern employed was a cycle of 110 kPa for 250 seconds→180 kPa for 250 seconds (0.002 Hz). The temperature in the incubator was kept at 37° C., and the $CO_2$ concentration was kept at 5% during the process including the pressure application step.

(1) To a square glass culture dish (0.8 cm$^2$), 0.4 mL of cell suspension with a density of 750,000 cells/mL was added, and the culture dish was then left to stand under atmospheric pressure for 1 day, followed by performing pressurization treatment for 1 day. To the culture dish, 0.4 mL of cell suspension was further added, and the culture dish was left to stand under atmospheric pressure for 1 day, followed by performing pressurization treatment for 2 days.

(2) To a circular glass culture dish (0.7 cm$^2$), 0.4 mL of cell suspension with a density of 500,000 cells/mL was added, and the culture dish was left to stand under atmospheric pressure for 1 day, followed by performing pressurization treatment for 2 days. To the culture dish, 0.4 mL of cell suspension was further added, and the culture dish was left to stand under atmospheric pressure for 1 day, followed by performing pressurization treatment for 1 day.

(3) To a circular glass culture dish (0.7 cm$^2$), 0.4 mL of cell suspension with a density of 750,000 cells/mL was added, and the culture dish was left to stand under atmospheric pressure for 1 day, followed by performing pressurization treatment for 2 days. To the culture dish, 0.4 mL of cell suspension was further added, and the culture dish was left to stand under atmospheric pressure for 1 day, followed by performing pressurization treatment for 1 day. To the culture dish, 0.4 mL of cell suspension was further added, and the culture dish was left to stand under atmospheric pressure for 1 day, followed by performing pressurization treatment for 2 days.

Figure 6:
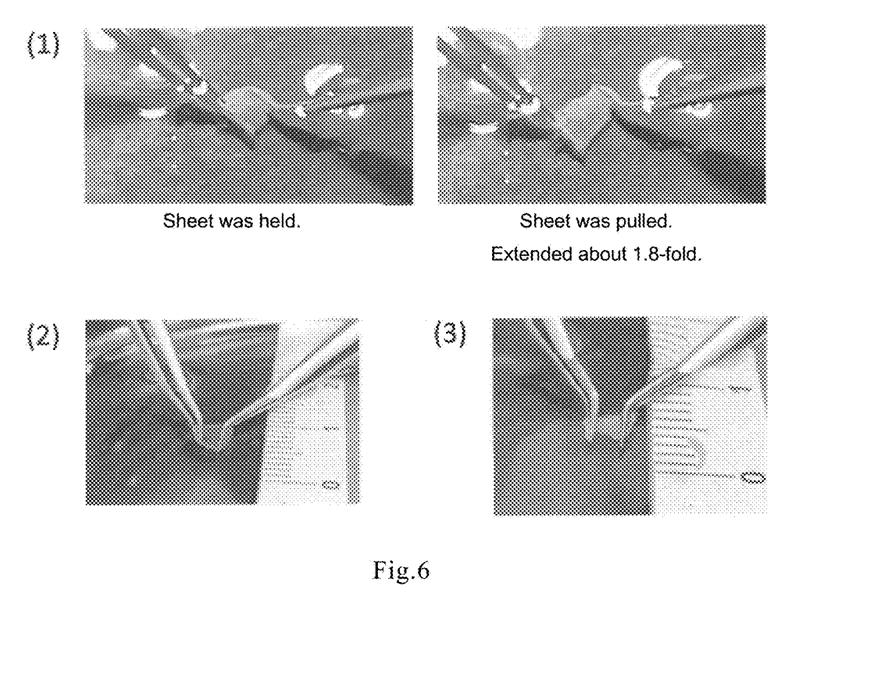
FIG. 6 shows photographs of cell aggregates obtained by the preparation method shown in FIG. 5, wherein addition of cells and application of pressure were repeated.

FIG. 6 shows photographs of cell aggregates prepared as described in (1) to (3) above. When the sheets were pulled using tweezers, the sheets extended about 1.8-fold without breakage. Thus, robust cell sheets could be prepared.

3. Preparation of Cell Aggregate by Pressure Application 3

Using human smooth muscle cells, cell aggregates were prepared by repeating addition of cells and pressurization treatment or by only repeating addition of cells and leaving the cells to stand under atmospheric pressure without pressurization treatment, and the obtained cell aggregates were compared with each other. As the cell container, a square glass culture dish (0.8 cm$^2$) was used. The culture dish was coated with fibronectin. The $CO_2$ concentration was kept constant at 5%, and the temperature was kept at 37° C.

Figure 7:
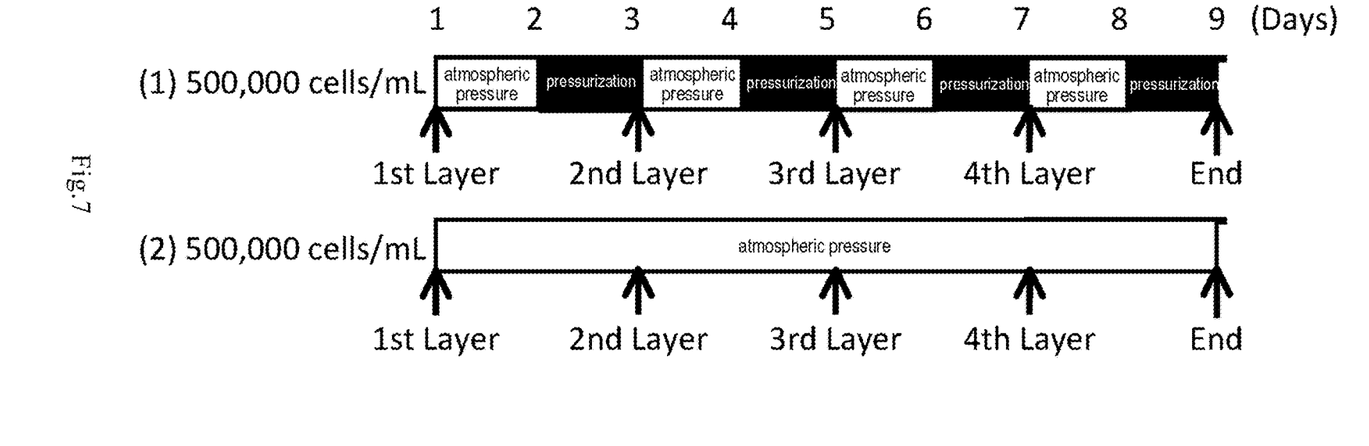
FIG. 7 shows a diagram illustrating the time courses of preparation methods carried out in Examples, wherein addition of cells and application of pressure were repeated, or only addition of cells was repeated without application of pressure.

(1) To a culture dish, 0.4 mL of cell suspension with a density of 500,000 cells/mL was added, and pressurization treatment was carried out as shown in (1) of FIG. 7. On Day 3, Day 5, and Day 7, 0.4 mL of cell suspension was further added. The pressurization was carried out by repeating a cycle of 110 kPa and 180 kPa at 0.002 Hz.

(2) To a culture dish, 0.4 mL of cell suspension with a density of 500,000 cells/mL was added, and culture was carried. On Day 3, Day 5, and Day 7, 0.4 mL of cell suspension was further added. The culture was carried out under atmospheric pressure throughout the culture period.

Figure 8:
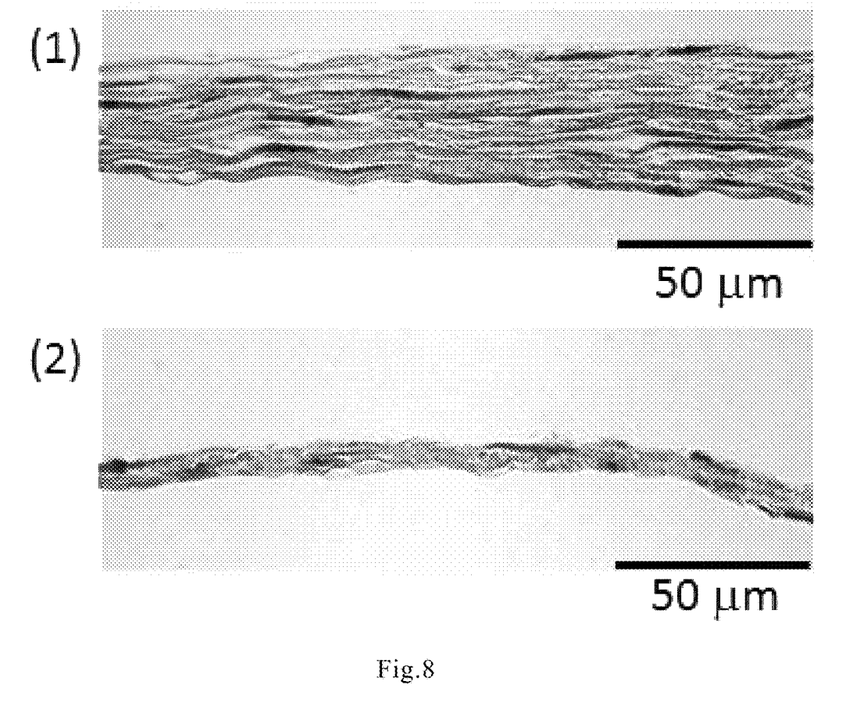
FIG. 8 shows HE-stained images of cell aggregates obtained by the preparation methods shown in FIG. 7.

Cell aggregates obtained by (1) and (2) were fixed with formalin, and their paraffin sections were prepared and stained with HE. FIG. 8 shows the HE-stained images. The cell aggregate of (1), which was prepared with pressurization, showed four or more layers of cells arranged in a laminar pattern. The cell aggregate of (2), which was prepared without pressurization, hardly showed layered cells, and no laminar pattern could be found.

4. Preparation of Cell Aggregate by Pressure Application 4

Figure 12:
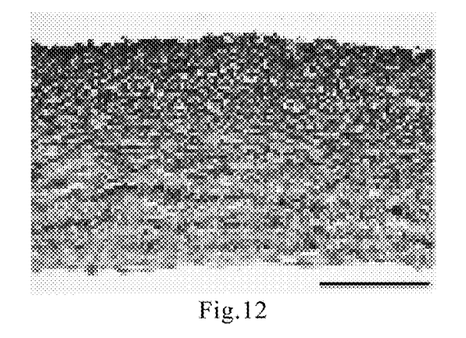
FIG. 12 shows an Elastica-van Gieson-stained image of a cell aggregate obtained by a preparation method in which addition of cells and application of pressure were repeated, which cell aggregate has 15 layers of cells. The scale bar represents 100 μm.

In a glass culture dish, 1,000,000 rat neonatal aortic smooth muscle cells were pressurized at 110-180 kPa at 0.002 Hz for 24 hours. On the next day, 1,000,000 cells were further added to the culture dish. During the treatment, the $CO_2$ concentration was kept constant at 5%, and the temperature was kept at 37° C. This process was repeated 15 times, and a cell aggregate having 15 layers was obtained one month later. FIG. 12 shows an image of an Elastica-van Gieson-stained section of the cell aggregate obtained. The scale bar represents 100 μm. The thickness of the cell aggregate was as large as more than 200 μm. Viable cells were stained with trypan blue and counted to find that the viable cell ratio was not less than 90%. Remarkable formation of elastic fibers in a laminar pattern was found, and two-fold or more extension could be observed in the tension test. These properties are comparable to those of human small-diameter vascular walls, and it could be confirmed that the obtained cell aggregate has very high robustness.

Figure 9:
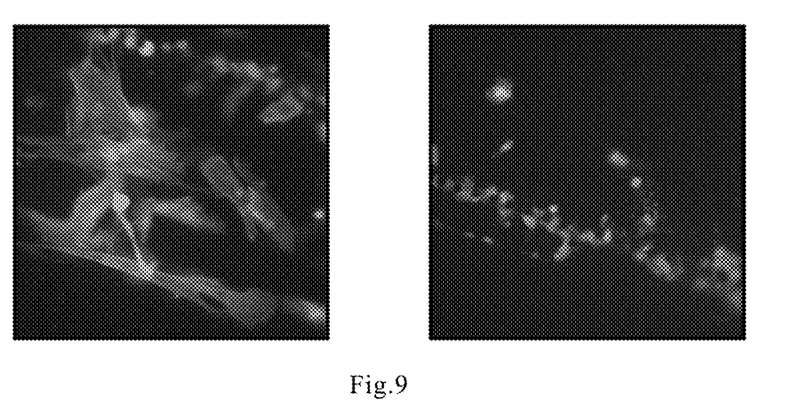
FIG. 9 shows the results of immunofluorescent staining of F-actin and cell nuclei in umbilical arterial smooth muscle cells to which pressure was applied in a microfluidic chip. Left panel: cells with application of pressure. Right panel: cells without application of pressure.

5. Influence of Pressurization Treatment on Cells (1) Pressure was applied (180 kPa) to monolayer human umbilical arterial smooth muscle cells in a microfluidic chip using a syringe pump, and the influence of the pressurization at the cellular level was investigated. As a result of immunofluorescent staining of F-actin and cell nuclei, it was found that the cells to which the pressure was applied (FIG. 9, left) showed a drastic increase in actin filaments as compared to cells to which pressure was not applied (FIG. 9, right).

Figure 10:
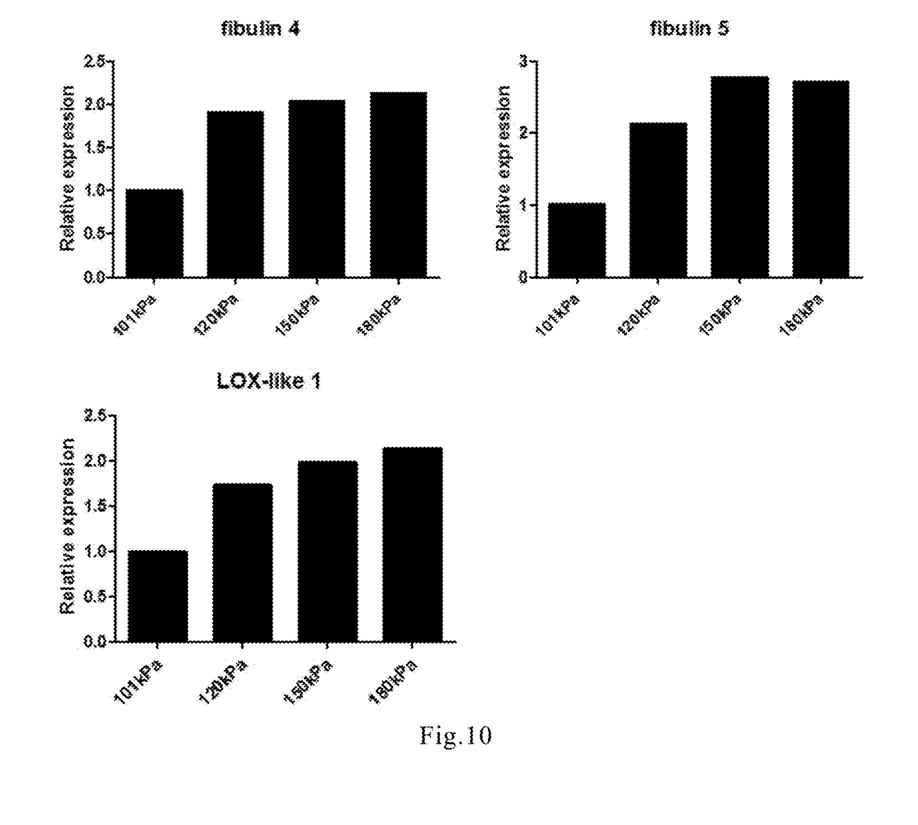
FIG. 10 shows the results of investigating the expression levels of extracellular matrix genes (fibulin 4, fibulin 5, LOX-like protein 1) in monolayer human umbilical arterial smooth muscle cells prepared by carrying out pressurization treatment at the pressures shown in the figure for 90 minutes and culturing the treated cells under atmospheric pressure for 24 hours.

(2) A human umbilical arterial smooth muscle cell suspension with a cell density of 1,000,000 cells/mL was subjected to monolayer culture in a petri dish. The cells were subjected to pressurization (periodic pressurization of "110 kPa for 10 seconds—180 kPa for 10 seconds") for 90 minutes, and then cultured under normal atmospheric pressure for 24 hours. Thereafter, RNA was collected from the cells, and extracellular matrix mRNAs were measured by real-time PCR. The results are shown in FIG. 10. All of the extracellular matrices showed increased expression levels due to the pressurization.

Actin filaments set up the skeleton of the cell, and are involved in adhesion of cells to each other. It is thought that the increases in the actin filaments and the extracellular matrices that occurred in the cells that have undergone the pressure application may have contributed to the aggregation and adhesion of the cells that occurred in a short time.

Figure 111:
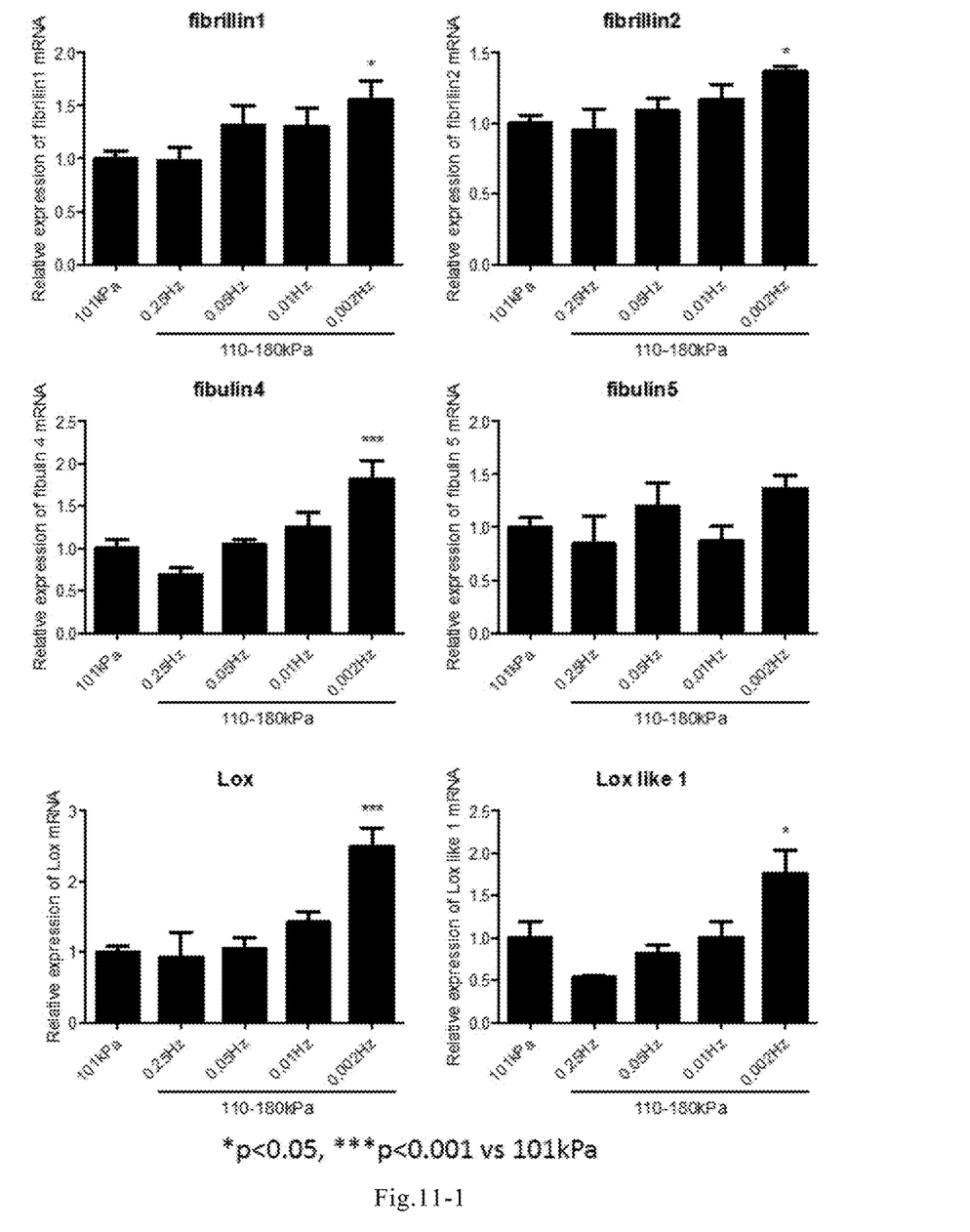
Figure 112:
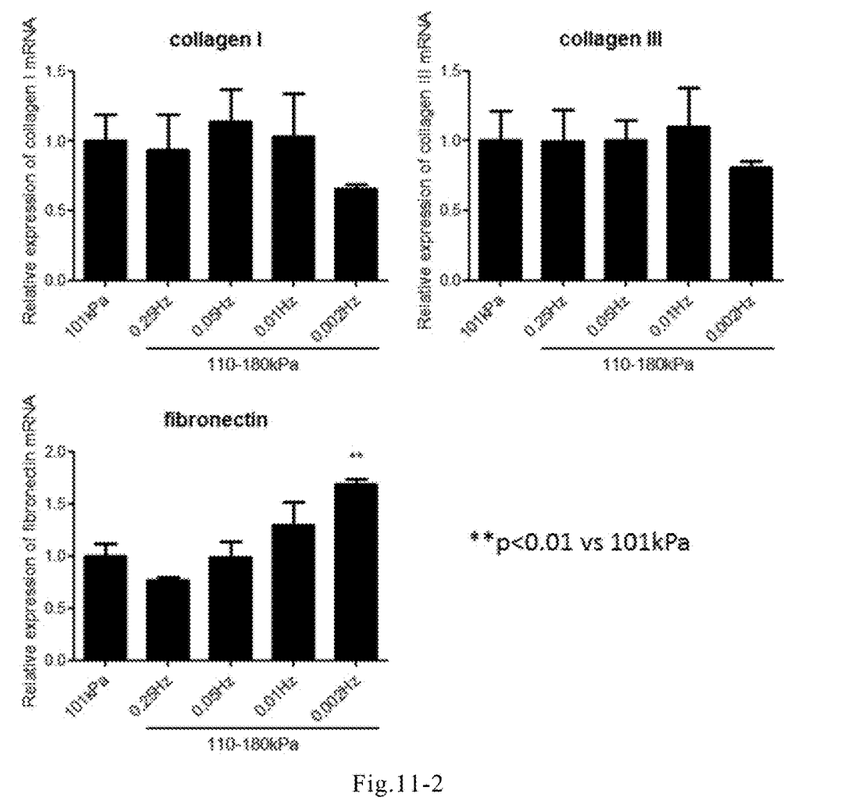

(3) The influence of the period of the pressurization cycle on the cells was investigated using different periods. In a 5-mL syringe, 650,000 human umbilical arterial smooth muscle cells were placed, and then cultured for 20 hours under atmospheric pressure (101 kPa), or under periodic pressure with the following cycle: 110 kPa for 2 seconds—180 kPa for 2 seconds (0.25 Hz); 110 kPa for 10 seconds—180 kPa for 10 seconds (0.05 Hz); 110 kPa for 50 seconds—180 kPa for 50 seconds (0.01 Hz); or 110 kPa for 250 seconds—180 kPa for 250 seconds (0.002 Hz). The resulting cell aggregates were subjected to measurement of the expression levels of various genes by real-time PCR. During the culture, the $CO_2$ concentration was kept constant at 5% in the case of 0.002 Hz, and kept constant at 3.6% in the cases of the other frequencies. The temperature was kept at 37° C. The results are shown in FIG. 11. Fibrillin 1, fibrillin 2, fibulin 4, fibulin 5, LOX, and LOX-like 1 are genes related to elastic fibers; collagen I and collagen III are subtypes of major collagen supporting the vascular wall; and fibronectin is a major extracellular matrix of the vascular wall and is a component of elastic fibers. As a result of the present study using the human umbilical arterial smooth muscle cells, although the changes in the pressurization period did not influence the expression levels of some of the genes, the expression levels showed a general tendency to increase as the period increases.

Figure 13:
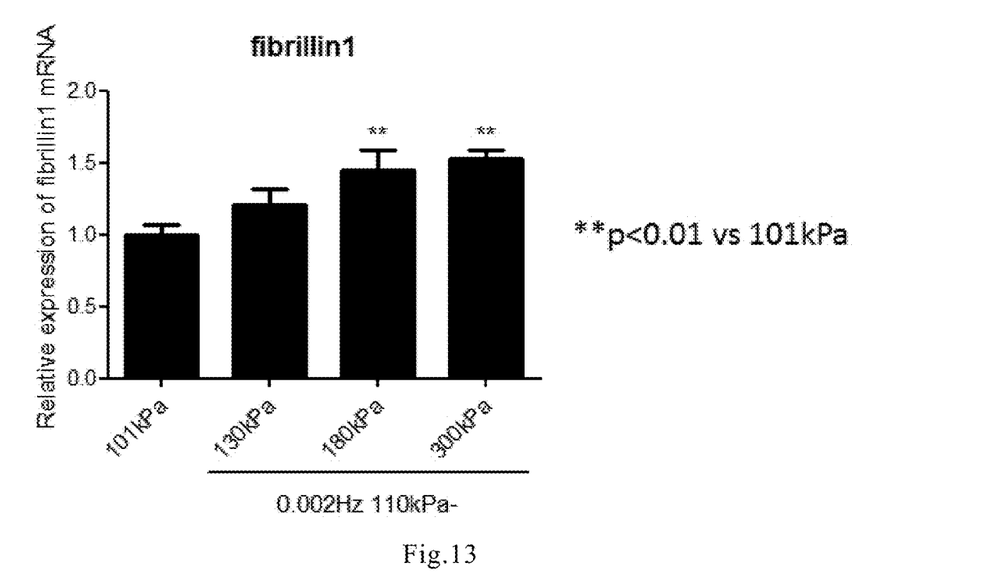
FIG. 13 shows the results of investigating the influence of the intensity of the applied pressure on cell aggregates. Human umbilical arterial smooth muscle cells were subjected to pressurization treatment for 20 hours by pressurization cycles with different higher pressures. Thereafter, the expression level of an extracellular matrix gene (fibrillin 1) was investigated. $**p<0.01$ vs 101 kPa.

(4) The influence of the pressure applied on the cells was investigated using different pressures. In a 5-mL syringe, 650,000 human umbilical arterial smooth muscle cells were placed, and the cells were kept under atmospheric pressure (101 kPa), or subjected to pressurization treatment for 20 hours with a period of 0.002 Hz in which the lower pressure was fixed at 110 kPa and the higher pressure was set at 130 kPa, 180 kPa, or 300 kPa. The resulting cells were subjected to measurement of the mRNA expression of the fibrillin 1 gene by real-time PCR. During the culture, the $CO_2$ concentration was kept constant at 5%, and the temperature was kept at 37° C. The results are shown in FIG. 13. It could be confirmed that the fibrillin 1 gene showed an increased expression level even in cases where a high pressure exceeding 180 kPa was applied.

DESCRIPTION OF SYMBOLS

2. Cell container
4. Pressure vessel
6. Regulator
8. Compressor
10. Incubator
12. Computer
14. Cell suspension

The invention claimed is:

1. A device for preparing a three-dimensional cell aggregate, said device comprising:
   a pressure vessel for holding a cell container in a gas phase therein;
   an incubator for holding at least the pressure vessel in a gas phase therein;
   a compressor communicating with the gas phase in the incubator, for compressing gas in the incubator to generate compressed gas;
   a regulator connected to the compressor and to the inside of the pressure vessel; and
   a computer which is connected to the regulator and gives instructions to the regulator to control intensity and pattern of pressure,
   wherein, when cells are provided in a cell container within the pressure vessel, pressure is applied to cells in the cell container by sending the compressed gas into the pressure vessel.

2. The device according to claim 1, wherein the computer gives instructions to carry out periodic pressurization.

3. The device according to claim 1, wherein the computer gives instructions to carry out periodic pressurization by changing at intervals of several seconds to several minutes or several hundred seconds.

4. The device according to claim 1, which does not contain a porous three-dimensional scaffold in said cell container.

5. The device according to claim 1, wherein the computer gives instructions to carry out periodic pressurization by alternating between high pressure and low pressure, the high pressure being selected from a range of 150 kPa to 100 MPa, the low pressure being equal to or higher than atmospheric and lower than said high pressure.

6. The device according to claim 5, wherein the high pressure is 150 kPa to 500 kPa.

7. The device according to claim 1, wherein the computer gives instructions to apply only atmospheric pressure to the cells in said cell container before application of pressure.

8. The device according to claim 1, wherein the cell container is a non-sealed container.

9. The device according to claim 1, wherein the cell container contains a surface treatment for cell adhesion.

10. The device according to claim 9, wherein the surface treatment is collagen coating or polylysine coating.

11. The device according to claim 1, wherein a $CO_2$ concentration of gas within the cell container is configured to be adjusted such that the pH of any cell suspension is maintained during any pressure application.

* * * * *